(12) United States Patent
Dubrovsky

(10) Patent No.: US 11,891,643 B2
(45) Date of Patent: Feb. 6, 2024

(54) METHODS AND SYSTEMS FOR MONOMER CHAIN FORMATION

(71) Applicant: SiPhox, Inc., Burlington, MA (US)

(72) Inventor: Michael Dubrovsky, Somerville, MA (US)

(73) Assignee: SiPhox, Inc.

( * ) Notice: Subject to any disclaimer, the term of this patent is extended or adjusted under 35 U.S.C. 154(b) by 224 days.

(21) Appl. No.: 17/337,931

(22) Filed: Jun. 3, 2021

(65) Prior Publication Data

US 2021/0381018 A1   Dec. 9, 2021

Related U.S. Application Data

(60) Provisional application No. 63/034,205, filed on Jun. 3, 2020.

(51) Int. Cl.
| | | |
|---|---|---|
| *C12P 19/34* | (2006.01) | |
| *C12N 9/22* | (2006.01) | |
| *C12N 15/11* | (2006.01) | |

(52) U.S. Cl.
CPC ............. *C12P 19/34* (2013.01); *C12N 9/22* (2013.01); *C12N 15/111* (2013.01); *C12N 2310/20* (2017.05)

(58) Field of Classification Search
CPC ......... C12P 19/34; C12N 9/22; C12N 15/111; C12N 2310/20; G01N 33/54373
See application file for complete search history.

(56) References Cited

U.S. PATENT DOCUMENTS

| | | |
|---|---|---|
| 2002/0150927 A1 | 10/2002 | Matray et al. |
| 2003/0207300 A1 | 11/2003 | Matray et al. |
| 2004/0265902 A1 | 12/2004 | Fricker et al. |
| 2005/0089940 A1 | 4/2005 | Pidaparthi et al. |
| 2008/0050743 A1 | 2/2008 | Sorge et al. |
| 2009/0155818 A1 | 6/2009 | Pidaparthi et al. |
| 2011/0207132 A1 | 8/2011 | Sintim |
| 2014/0170654 A1 | 6/2014 | Landegren et al. |
| 2019/0144925 A1 | 5/2019 | Arab |
| 2020/0040376 A1 | 2/2020 | Russel et al. |
| 2020/0363413 A1 | 11/2020 | Brennan et al. |

FOREIGN PATENT DOCUMENTS

| | | | |
|---|---|---|---|
| CN | 112725343 A | 4/2021 | |
| WO | 2002097112 | 12/2002 | |
| WO | 2004063700 | 7/2004 | |
| WO | WO-2020028180 A1 * | 2/2020 | ............. C12N 15/11 |

OTHER PUBLICATIONS

Lawrie et al. Phys. Status Solidi A 206, No. 6, 1339-1342, 2009 (Year: 2009).*
Lue et al. 2011 International Conference on Biomedical Engineering and Informatics (Year: 2011).*
Mukundan H et al. 2009;9(7):5783-809 (Year: 2009).*
Illumina (Product Insert Description entitled "Illumina Sequencing Technology," 2010) (Year: 2010).*
Fodor, S et al. (1991)Science251,767-773 (Year: 1991).*
Mudumba S et al. J Immunol Methods. Sep. 2017;448:34-43 (Year: 2017).*
Karymov et al. Sensors and Actuators B: Chemical, vol. 29, Issues 1-3, Oct. 1995, pp. 324-327 (Year: 1995).*
Liu et al. , DNAzyme-based fluorescent microarray for highly selective and sensitive detection of lead(II)†, Dec. 31, 2013.
Mingdi et al., Nanoscale assembly line composed of dual DNA-machines enabling sensitive microRNA detection using upconversion nanoparticles probes , Dec. 31, 2021.
Juskowiak et al. , Nucleic acid-based fluorescent probes and their analytical potential, Dec. 31, 2013.
Turcatti, et al.,, A new class of cleavable fluorescent nucleotides: synthesis and optimization as reversible terminators for DNA sequencing by synthesis, Dec. 31, 2008.

* cited by examiner

*Primary Examiner* — Neil P Hammell
*Assistant Examiner* — Douglas Charles Ryan
(74) *Attorney, Agent, or Firm* — Caldwell Intellectual Property Law

(57) ABSTRACT

Aspects relate to systems and methods for high-contrast cleavage detection. An exemplary method includes a plurality of probes, wherein at least a probe of the plurality of probes comprises a high-contrast agent, a waveguide configured to propagate an electromagnetic (EM) wave, wherein the waveguide includes a surface upon which the plurality of probes are immobilized, wherein the surface is configured to provide communication between the EM wave and the high-contrast agent, a primary cleaving agent proximal the plurality of probes, wherein the primary cleaving agent and the plurality of probes are configured to selectively cleave the at least a probe as a result of the primary cleaving agent being in presence of an analyte, and a sensor in communication with the waveguide and configured to detect cleaving of the at least a probe by way of the EM wave.

18 Claims, 9 Drawing Sheets

METHODS AND SYSTEMS FOR MONOMER CHAIN FORMATION

CROSS-REFERENCE TO RELATED APPLICATIONS

This application claims the benefit of priority of U.S. Provisional Patent Application Ser. No. 63/034,205, filed on Jun. 3, 2020, and titled "HIGH CONTRAST CLEAVAGE SENSING METHOD, CHEMICAL FACTORY AND SENSOR ON-A-CHIP USING INTEGRATED PHOTONICS, MEMS, MICROFLUIDICS AND ELECTRONIC CIRCUITS," which is incorporated by reference herein in its entirety.

FIELD OF THE INVENTION

The present invention generally relates to the field of on-chip chemical reactors. In particular, the present invention is directed to monomer chain formation.

BACKGROUND

Presently, DNA-oligo synthesis is limited by poor yields, in part because of the many steps of base addition required to construct a chain. For example, if the yield of each base addition is high at 99.5%, 200 polymerization steps, will only yield about 36% correct 200-base oligos. This current yield limitation prevents the reliable scale-up of DNA-oligo synthesis.

SUMMARY OF THE DISCLOSURE

In an aspect, a method of monomer chain formation includes immobilizing, using a surface of a waveguide, a monomer chain, providing a first monomer, wherein the first monomer comprises a capping agent, attaching the first monomer to the monomer chain, and detecting, using a sensor in communication with the waveguide, presence of the first monomer.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Aspects of the present disclosure allow for high yield construction of monomer chains. Exemplary embodiments illustrating aspects of the present disclosure are described below in the context of several specific examples.

The ability to control chemical processes at or near the surface of a chip has many applications including nanofabrication of surface coatings, fabrications of polymers, oligomers (including DNA/RNA) and chemical catalysis in general. Surface functionalization of materials like Silicon and glass may be used for biosensing and many other applications. Fabrication of polymers can especially be useful if the polymers can be sequence-controlled, for example without limitation proteins with specific amino acid sequences and DNAs or RNAs with specific nucleotide sequences. Additionally controlling reaction kinetics, secondary bonding/folding of polymers and monitoring the fidelity and progress of reactions is very useful.

Figure 1:
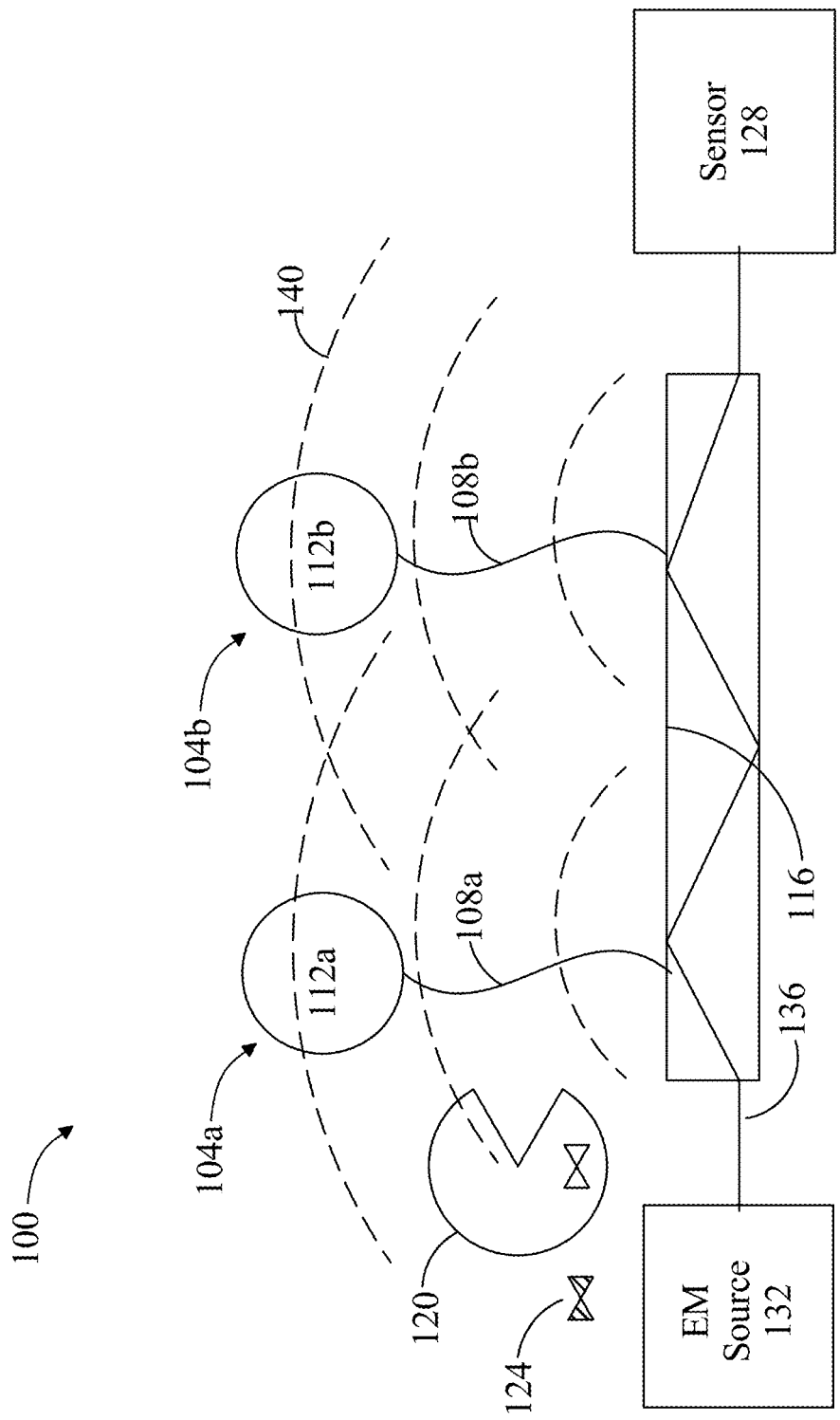
FIG. 1 is a block diagram illustrating an exemplary system for high-contrast cleavage detection.

Referring now to the drawings, FIG. 1 illustrates an exemplary system 100 for high-contrast cleavage detection. System 100 may include a plurality of probes 104a-b. As used in this disclosure, a "probe" is a selectively cleavable substance 108a-b, such as without limitation a molecule, having a contrast agent 112a-b. A probe may be referred interchangeably as a reporter probe and/or a standardized reporter probe. A "cleavable substance," as used in this disclosure is any substance which may be cleaved. In some cases, cleavable substance 108a-b may include a polymer, such as without limitation a polymer, which may include a biopolymer such as without limitation an amino acid chain, ribonucleic acid (RNA) and/or deoxyribonucleic acid (DNA). As used in this disclosure, a "contrast agent" is a substance that is detectable using any sensing methodology, such as without limitation electrical sensing, magnetic sensing, optical sensing, chemical sensing and the like. A contrast agent may be referred to interchangeably as a label. In some cases, contrast agent 112a-b may include at least one of metal nanoparticles, such as without limitation gold. Alternatively or additionally, contrast agent 112a-b may include a fluorophore and/or a chemical dye. In some cases, contrast agent 112a-b may include an optically active and/or conductive or magnetic component, which may be detectable using electronical and/or magnetic circuit elements. Contrast agent 112a-b may facilitate detection of cleavage of at least a probe 104a-b.

With continued reference to FIG. 1, in some cases, plurality of probes 104a-b may be immobilized, for instance without limitation upon a surface 116. As used in this disclosure, "immobilized" refers to an attribute of no substantially relative movement between two relata, for example at least a probe and a surface. In some cases, surface may be functionalized. For example, surface may be coated or otherwise treated in order to facilitate bonding, such as without limitation covalent bonding. In some exemplary embodiments, surface may be functionalized with streptavidin and/or avidin and at least a probe may comprise biotin, thereby facilitating immobilization. For instance, Avidin and other biotin-binding proteins, including Streptavidin and NeutrAvidin protein, have an ability to bind up to 5 biotin molecules, thereby facilitating immobilization. The Avidin-biotin complex is a strong non-covalent interaction ($K_d=10^{-15}$M) between a protein and ligand. Bond formation between biotin and Avidin can be very rapid, and once formed, may be unaffected by extremes of pH, temperature, organic solvents and other denaturing agents. These features of biotin and Avidin—features that are shared by Streptavidin and NeutrAvidin Protein—are useful for immobilization. In some cases, surface 116 may include a waveguide. As used in this disclosure, a "waveguide" is an element configured for propagation of electromagnetic waves. In some cases, a waveguide may be configured to propagate an EM wave by any of total internal reflection, attenuated total internal reflection, and/or frustrated internal reflection. In some cases, a waveguide may be configured to propagate an EM wave through reflection, transmission, and/or scatter. In some cases, waveguide may be configured to propagate EMR through surface plasmons, for example without limitation through surface plasmon resonance. Surface plasmon resonance (SPR) may include resonant oscillation of conduction electrons, for instance at an interface between negative and positive permittivity material stimulated by incident light. SPR may alternatively or additionally be used to measure adsorption of material onto planar metal, such as without limitation gold or silver, surfaces or onto a surface of metal nanoparticles, for instance and without limitation if metal nanoparticles are used as contrast agent 112a-b as described above.

With continued reference to FIG. 1, in some cases, system 100 may include a primary cleaving agent 120. A primary cleaving agent 120 may be located proximal to plurality of probes 104a-b. As used in this disclosure, a "cleaving agent" is any substance, electromagnetic signal generator, or other phenomenon or generator thereof which is capable of cleaving a probe, for instance and without limitation by cleaving and/or severing selectively cleavable substance 108a-b. In some embodiments, cleaving agent may include an enzyme. For example, cleaving agent may include CRISPR enzymes that may be activated by a target polymer (e.g., RNA) or any analyte of interest.

With continued reference to FIG. 1, clustered regularly interspaced short palindromic repeats (CRISPR) may include a family of DNA sequences, for example as found in genomes of prokaryotic organisms. In some cases, CRISPR sequences may be derived from DNA fragments of bacteriophages that had previously infected a prokaryote. In some cases, CRIPT enzymes may be used to detect and destroy DNA from similar bacteriophages during subsequent infections. An exemplary CRISPR enzyme, Cas9 (or "CRISPR-associated protein 9") is an enzyme that may use CRISPR sequences as a guide to recognize and cleave specific strands of DNA that are complementary to the CRISPR sequence. Cas9 enzymes together with CRISPR sequences can be used to edit genes within organisms. This editing process has a wide variety of applications including basic biological research, development of biotechnological products, and treatment of diseases.

With continued reference to FIG. 1, in some cases, primary cleaving agent 120 and/or plurality of probes 104a-b are configured to selectively cleave at least a probe of the plurality of probes 104a-b, as a result of the primary cleaving agent 120 being in presence of an analyte 124. As used in this disclosure, "selective cleaving" is an action of purposeful cleaving a cleavable substance; for example, selective cleaving may include cleaving of the cleavable substance conditionally. used in this disclosure, an "analyte" is any substance that is of interest, for example during an analytical chemistry procedure. In some cases, an analyte may include a chemical species. Additionally or alternatively, an analyte may include a pure substance, such as without limitation 24 karat gold, NaCL, water, and the like. In some cases, a cleaving agent may cleave at least a probe and/or cleavable substance, removing it from surface 116, for instance when an analyte 124 of interest binds to or is otherwise detected by the cleaving agent. Once cleaving agent is activated, it may cleave probes from surface 116, thereby leading to a detectable signal (for example by way of resonance, absorbance, interference resistance changes or other detectable changes near the sensing surface as described in further detail below).

Still referring to FIG. 1, in some embodiments, cleavage of at least a probe may be caused by analyte 124 of interest. Alternatively or additionally, cleavage may be facilitated via a chemical in solution and/or from electromagnetic radiation (e.g. UV light). For example, cleaving agent may include a chemical in solution and/or an electromagnetic radiation, for example light or radiative transmission of heat at certain wavelengths. In some cases, sensor 128 may detect removal of probe 104a-b. In some cases, at least a probe 104a-b may become mobilized, which as used herein may signify removal from immobilization with surface 116 by way of light, heat, other general environmental changes, or other changes local to probe 104a-b that can cause the probe to detach. In a nonlimiting example, at least a probe 104a-b may include UV cleavable linkages and/or heat-disassociated bonds and cleaving agent may comprise a UV light and/or heat source, respectively. Sensor 128 may include one or more of an electronic, magnetic, MEMS, optical, or optoelectronic device.

In some embodiments, system 100 may sense analytes 124 in solution that are exposed to surface 116 by sensing selective cleavage of probe by high-contrast agent in presence of analytes. For instance, and without limitation, at least a probe may be cleaved as a result of a chemical or enzyme (i.e., cleaving agent 120) associated with, activated, and/or catalyzed by a target analyte 124. In one non-limiting example, cleaving agent may include an enzyme such as a CRISPR and/or associated enzyme, a Toehold Switch RNA detection produced enzyme, or protein that may cleave reporter probes 104a-b at selectively cleavable substance 108a-b such as RNA strands immobilized on surface 116 of a sensor 128 or other device. In some cases, cleaving agent 124 may be activated upon exposure to an analyte 124 of interest in solution, thereby cleaving immobilized reporter probes 104a-b; for instance, the cleaving agent may be activated by proximity to and/or contact with analyte 124 of interest, such as without limitation interaction with an active site of cleaving agent.

With continued reference to FIG. 1, in some embodiments, Secondary cleaving agent may be selectively cleavable and/or a cleaving agent may cleave secondary cleaving agent upon exposure to analyte as described above. Alternatively or additionally, in some cases, secondary cleaving agent may be non-selective, so that it cleaves probes without requiring an analyte, such as without limitation a primary analyte or a secondary analyte. In some additional embodiments, a tertiary cleaving agent may be immobilized as well, for instance without limitation upon a surface 116. Tertiary cleaving agent may be cleavable, and thus mobilized by, one or more of a primary cleaving agent and a secondary cleaving agent. So, in some non-limiting cases, secondary cleaving agent may be mobilized by exposure to a primary cleaving agent, for example in presence with a primary analyte; and the secondary cleaving agent may then cleave, thereby releasing probes and/or tertiary cleaving agents, which in turn cleave and mobilize more probes and/or cleaving agents, thus generating a chain reaction, cascade, or avalanche.

Still referring to FIG. 1, in some embodiments, cleaving of probes 104a-b may include a multistep cleaving process; for example system 100 may include a secondary cleaving agent. Secondary cleaving agent may, as a non-limiting example, be immobilized using a selectively cleavable substance as described above. In some cases, secondary cleaving agent may be immobilized upon surface 116. Alternatively or additionally, secondary cleaving agent may be located proximal plurality of probes 104a-b. In some cases, primary cleaving agent 120 may be further configured to cleave a secondary cleaving agent when in presence of analyte 124, thereby mobilizing the secondary cleaving agent proximal the plurality of probes. In some cases, secondary cleaving agent may be configured to cleave at least a probe of plurality of probes 104a-b. In some implementations, secondary cleaving agents may be surface bound or otherwise immobilized, locked, and/or inactivated by a cleavage linkage and mobilized, removed, unblocked, and/or activated by way of cleavage, for example with a primary cleaving agent 120 when an analyte 124 is sensed. In some cases, this technique may be useful to amplify a detectable signal from a small cleavage event associated with a small amount of analyte 124, which may cascade into the cleavage of a large number of reporter probes that may be more easily detectable by sensor 128. In other words, in some cases, secondary cleaving agents may create an amplification as a result of one primary cleaving agent (e.g. CRISPR) after becoming activated by analyte 124 of interest, cleaves many secondary cleaving agents, which then go on to cleave probes 104a-b, for example from a sensing surface 116. In some cases, cleavage may also occur in solution or on surfaces in a way that either releases/activates secondary cleaving agents (e.g. for cleaving probes from sensing surfaces) or high contrast probes that go on to bind to sensing surfaces.

With continued reference to FIG. 1, in some cases, system may include a sensor 128. Sensor 128 may be configured to detect at least a probe of plurality of probes 104a-b. In some cases, sensor 128 may be configured to only detect substantially cleaved probes. Alternatively or additionally, in some cases, sensor 128 may be configured to only detect substantially uncleaved probes. As used in this disclosure, a "sensor" may include any device that is configured to detect a phenomenon, for example a phenomenon associated with at least a probe. A sensor may include any type of sensors, including without limitation sensors configured to detect electrical phenomenon, chemical phenomenon, and/or optical phenomenon. In some embodiments, sensing of cleavage of at least a probe 104a-b may be performed on a surface in an electronic, optical, MEMS, or optoelectronic device. General sensing techniques include but are not limited to using a doped optical waveguide or electrodes near a waveguide to sense an optical change or resistance change, respectively, after at least a probe has been cleaved. In some examples, optical changes may be detected using surface plasmon resonances, Mach-Zehnder interferometers, spiral waveguides, Bragg gratings, and/or photonic crystals or magnetic dielectric mirrors. In some embodiments, sensor 128 may be collocated with surface 116; said another way, the surface 116 may include the sensor 128 or a detection path between the sensor 128 and the at least a probe. In some embodiments, sensor 116 is configured to be within electrical communication with at least a probe. For example in some embodiments, contrast agent 112a-b may include an electrically active (e.g., conductive, resistive, shielding, and the like) material, which is able to be sensed by an electrical sensor 128. As used in this disclosure, "communication" is used to refer to a causal or sensed relationship between two relata; for example just as two people talking on over a telephonic may be said to be in communication with one another, a photosensor may be said to be in communication with a probe which is reflecting fluorescing or otherwise transmitting a light, which the photosensor is detecting. According to some other exemplary embodiments, sensor 128 may include a waveguide that is configured to be within evanescent wave communication with the at least a probe.

With continued reference to FIG. 1, in some exemplary cases, system 100 may include a waveguide which constitute a surface 116 upon which a plurality of probes 104a-b are immobilized. In some cases, waveguide may include an optical waveguide configured to propagate EM waves, such as without limitation light by way of total internal reflection. Accordingly, in some cases, waveguide may have an index of refraction that is substantially greater than a medium surrounding waveguide. For example, in some exemplary cases, waveguide may comprise sapphire and have an index of refraction which is greater than 2 and medium surrounding the waveguide may comprise water and have an index of refraction of about 1.4. System 100 may include a light source 132 configured to emit a light 136, which may be emitted into and/or at waveguide. As used in this disclosure, a "light source" is any device configured to emit a light. A light source may include a coherent light source and/or an incoherent light source. Non-limiting exemplary light sources include lasers, light emitting diodes (LEDs), organic LEDs (OLEDS), light emitting capacitors, incandescent lamps, fluorescent lamps, and the like. Light 136 may be coupled into waveguide and propagate within waveguide, for example and without limitation using total internal reflection. In some cases, light 136 may exit waveguide and be detected by a sensor 128 upon exiting waveguide. Waveguide may include any structure that may guide waves, such as electromagnetic waves or sound waves, by restricting at least a direction of propagation of the waves. Waves in open space may propagate in multiple directions, for instance in a spherical distribution from a point source. A waveguide may confine a wave to propagate in a restricted sent of directions, such as propagation in one dimension, one direction, or the like, so that the wave does not lose power, for instance to the inverse-square law, while propagating, and/or so that the wave is directed to a desired destination such as a sensor, light detector, or the like. In an embodiment, a waveguide may exploit total reflection at walls, confining waves to the interior of a waveguide. For example, waveguide may include a hollow conductive metal pipe used to carry high frequency radio waves such as microwaves. Waveguide may include optical waveguides that when used at optical frequencies are dielectric waveguides whereby a structure with a dielectric material with high permittivity and thus a high index of refraction may be surrounded by a material with a material with lower permittivity. Such a waveguide may include an optical fiber, such as used in fiberoptic devices or conduits. Optical fiber may include a flexible transparent fiber made from silica or plastic that includes a core surrounded by a transparent cladding material with a lower index of refraction. Light may be kept in the core of the optical fiber by the phenomenon of total internal reflection which may cause the fiber to act as a waveguide. Fibers may include both single-mode and multi-mode fibers. Acting as a waveguide, fibers may support one or more fined transverse modes by which light can propagate along the fiber. Waveguides may be made from materials such as silica, fluorozirconate, fluoroaluminate, chalcogenide glass, sapphire, fluoride, and/or plastic. Sensors 128 placed along waveguide may include any photon detector. In some cases, an output of optical waveguide may be coupled to a photodetector. Sensor 128 may include any optical or EM wave sensor, including without limitation a photosensor, a photodetector, a thermopile, a pyrolytic sensor, a photodiode, avalanche photodiode (APD), single photon avalanche photodiode (SPAD), and the like.

In some cases, and with further reference to FIG. 1, sensor 128 may be communicative with a circuit, for example without limitation an analog circuit. Circuit may take as input a signal from sensor 128 and process the signal. In some cases, one or more optical elements and/or optical systems may be used to couple light 136 into and/or out from waveguide. For example, coupling lenses having a numerical aperture selected based upon acceptable entrance angle and/or cross-sectional area of waveguide may be used to couple substantially collimated light 136 into waveguide and/or substantially collimate light 136 after exiting the waveguide. Circuit may include analog and/or digital circuit elements. Exemplary non-limiting analog elements, include operational amplifiers, comparators, amplification circuits, and the like. In some cases, circuit may include an analog circuit interfaced with a digital circuit, for example without limitation by way of an analog to digital (A/D) converter. Alternatively or additionally, an analog circuit may be interfaced with a digital circuit by way of a resistive divider, such as without limitation a Wheatstone bridge. Alternatively or additionally, analog circuit may be interfaced with a digital circuit by way of at least a control terminal of transistors (or other digital elements), which are configured to trip (or otherwise digitally indicate) a certain voltage threshold to configured to be indicative of a change in digital state. In some cases, circuit may include a digital circuit. Digital circuit could be any combinatorial or sequential circuit including logic gates, registers, and the like. Digital circuit may include a microprocessor, microcontroller, or the like. Digital circuit may include connection to a memory. In some embodiments, digital circuit may include or interface with at least a computing device. Computing device may include any computing device described in this disclosure, for example with reference to FIG. 9. In some cases, system 100 may be configured with aid of a computing device to perform any methods, steps, and/or processes described in this disclosure automatically.

With continued reference to FIG. 1, Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. Computing device may be implemented using a "shared nothing" architecture in which data is cached at the worker, in an embodiment, this may enable scalability of system 100 and/or computing device.

With continued reference to FIG. 1, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, in some cases, an evanescent wave 140 may result from EM wave 136 propagation within waveguide. An evanescent wave 140 may also be referred to as an evanescent field 140. An evanescent wave 140 may exhibit a rapidly decaying (or vanishing) field amplitude in a certain spatial direction, for example orthogonal to surface 116 of waveguide. In some cases, an evanescent wave 140 may not contribute to energy transport in a spatial direction such as a direction in which evanescent wave 140 exhibits a rapidly decaying or vanishing field amplitude, although in some cases a Poynting vector (averaged over one oscillation cycle) may have non-zero components in other directions. Evanescent wave 140 may be used to detect at least a probe. In some cases, a light signal 136 detected by sensor 128 may indicate presence and/or absence of probes. For example, an attenuated light signal 136 may indicate that at least a probe having a highly absorbent contrast agent is proximal to surface 116, as the attenuated light signal may result from evanescent wave 140 coupling, for instance via absorption, into contrast agent. As an evanescent wave 140 "vanishes" along a certain direction, its field amplitude, and therefore ability to be used for sensing, may diminish drastically as distance away from surface 116 increases. For example, depending upon parameters, such as index of refraction, light 136 wavelength, light 136 coupling angle, to name a few, an evanescent wave 140 may practically propagate less than 100 μm from surface, less than 10 μm from surface 116, or even less than 1 μm from service. In some cases, spatial selectivity affording by the aforementioned vanishing characteristic of evanescent waves 140 may be used to substantially sense only immobilized probes and/or only cleaved (i.e., mobilized) probes.

Still referring to FIG. 1, in some embodiments, plurality of probes 104a-b may be engineered to enhance a detected signal generated by cleavage. In some cases, binding of analyte 124 to surface 116 may directly generate a signal detectable by sensor 132. Sensor 132 detection may be performed by immobilizing at least a probe on a surface 116 of a waveguide, such that an evanescent field 140 interacts with the probes. Alternatively or additionally, any method or combination of surface methods (e.g. electrical and/or optical) may be used to detect cleavage of probes, including without limitation transistors, nanopores, surface plasmon resonant thin films or particles, surfaces used for SERS spectroscopy, or electrical resistance-based sensors. In some embodiments, cleavage of at least a probe may be sensed directly as described above, for instance without limitation by a change in response of a ring resonator or optical waveguide where plurality of reporter probes 104a-b were immobilized prior to cleavage. Alternatively or additionally, in some embodiments, at least a cleaved probe is detected by sensor 128. For example, in some cases, cleaved reporter probes may migrate away and be detected by sensor 128 elsewhere in system 100. In some cases, cleaved probes may migrate to and bind to a sensing surface, for example without limitation by way of diffusion and/or mixing. In some examples, cleaved probes may be designed for strong binding affinity to a sensing surface. In a non-limiting example, contrast agent 112a-b may include surface-functionalized gold particles which are functionalized with biotin and designed to bind to a surface functionalized with Streptavidin.

Still referring to FIG. 1, in some embodiments, system 100 may be used to sense activity and/or reaction kinetics associated with reaction, for example a reversible reaction with a biomolecule and/or enzyme. In some cases, surface 116 may be functionalized with an agent a biomolecule reacts with. A binding event associated with this reaction may be detected, for example without limitation by way of an optical resonance shift. In some cases, binding may result in a molecular complex falling apart and/or being broken. Detection of molecular complex breaking may be detected as a cleavage, for example as described above. In some cases, contrast or detected signal may increase by labeling a component of reaction using a contrast agent 112a-b.

Still referring to FIG. 1, in some embodiments, system 100 may additionally include a microfluidic channel. Microfluidic channel may be configured to permit a solution to flow through microfluidic channel and/or to store a solution. In some cases, solution may include at least one of a cleaving agent 120 and analyte 124. As used in this disclosure, a "microfluidic channel" is a fluidic pathway having a characteristic width less than 10 mm. A microfluidic channel may be consistent with channels used for fluidic communication in microfluidic chips and/or microfluidic circuits. In some cases, a fluidic channel of any size may be configured to permit a solution to flow through microfluidic channel and/or to store a solution. In some cases, a sample fluid may be split up into separate chambers, each containing a different cleaving agent (in a dried state or added via a different fluid input channel/port) with a different target analyte. In some cases, this may allow testing of a single sample for different analytes in parallel without interference. Alternatively or additionally, in some cases, testing may be performed on single sample in series, where the sample flows first over a first sensing surface containing a first cleaving agent, then flows into a chamber with a second cleaving agent, and so on (e.g. each chamber containing one or more sensing surfaces with cleavable probes). In some embodiments, separate optical system with distinct enzyme, splitting sample fluid may be used for both redundant testing by increasing sensitivity and/or specificity and multiplexing tests for multiple pathogens which may be advantageous for facile widespread testing.

Figure 2:
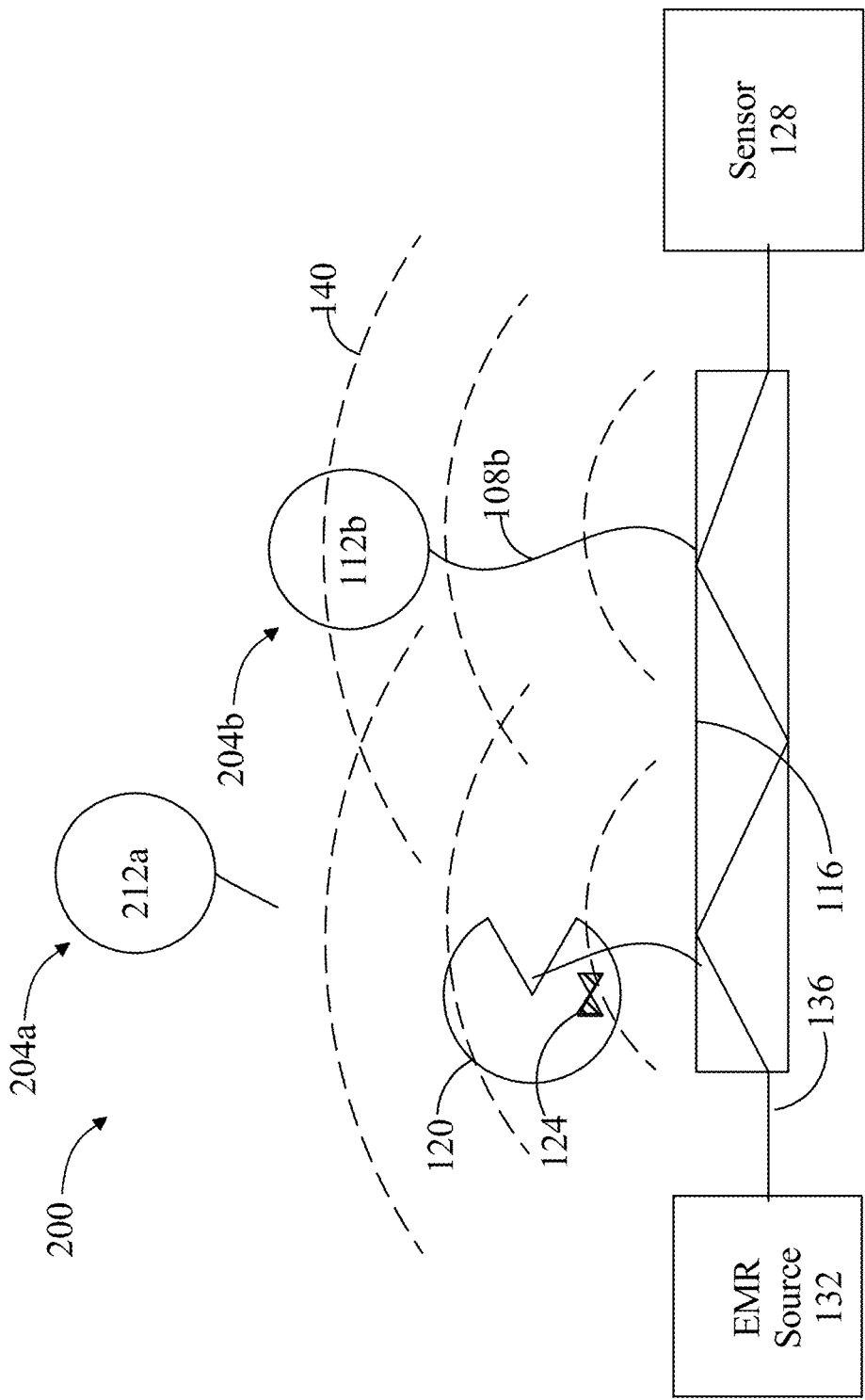
FIG. 2 is a block diagram of an exemplary system for high-contrast cleavage detection during a cleavage event.

Referring now to FIG. 2, an exemplary system 200 for high contrast cleavage sensing is illustrated in presence of cleavage. As can be seen in FIG. 2, analyte 124 has activated primary cleaving agent 120 which has cleaved a first cleaved probe 204A. First cleaved probe 204A, now mobilized, has dispersed from surface 116 and is no longer within evanescent wave 140 communication with sensor 128, therefore high contrast agent 212A of first cleaved probe 204A is no longer detected by sensor 116.

Figure 3:
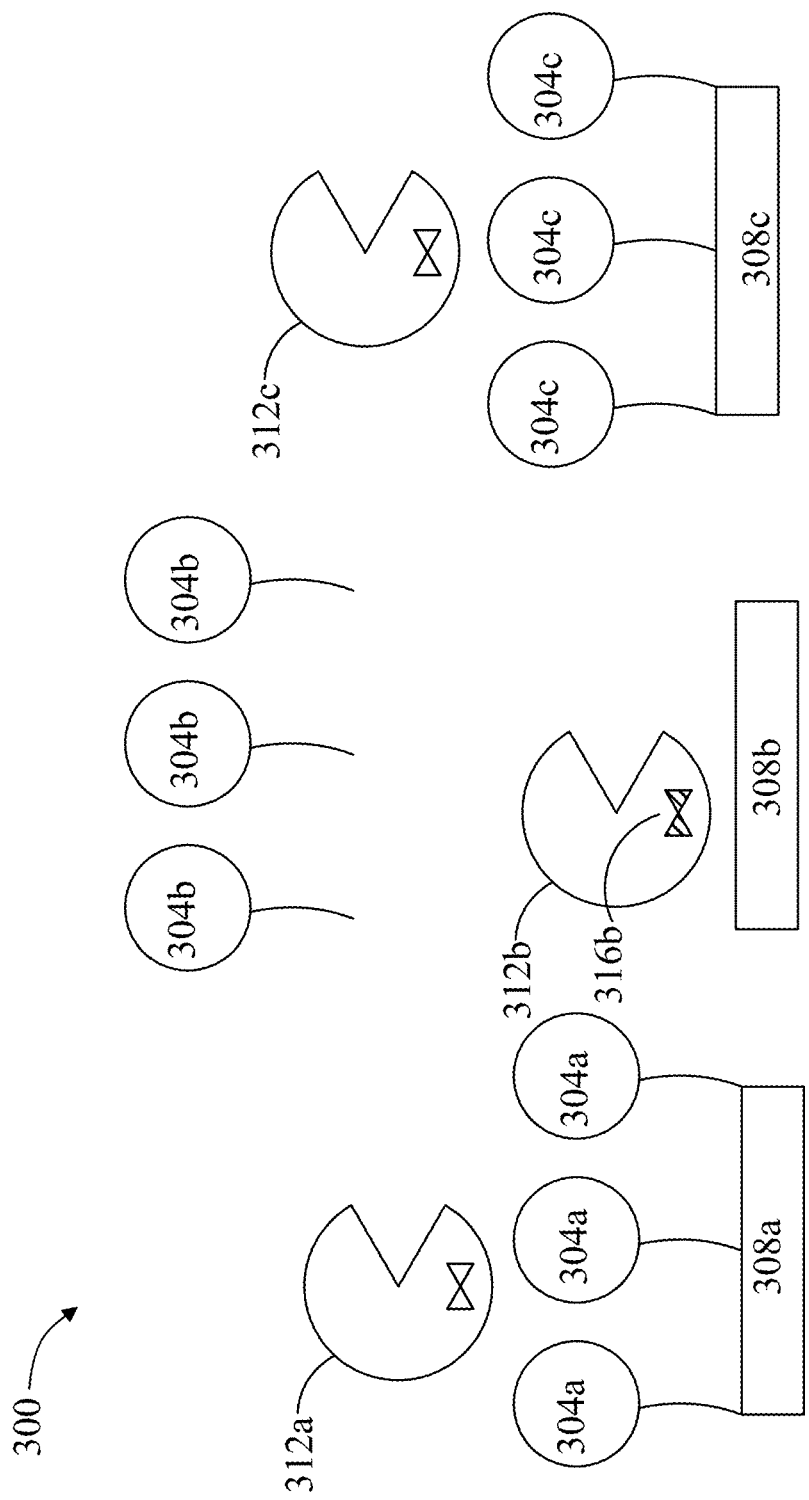
FIG. 3 is a block diagram depicting an exemplary system for selective high-contrast cleavage detection.

Referring now to FIG. 3, an exemplary system 300 for high contrast selective cleavage sensing is illustrated. In some embodiments, system 300 may be used to selectively sense a number of a target analytes. For example, exemplary system 300 is shown for illustrative purposes only as being configured to selectively sense for 3 different analytes "a," "b," and "c." System may have some number of different probe types; for instance, and solely as an illustration, system may include 3 different pluralities of probes 304a-c, each of which is configured to be cleaved as a result of presence from one of three different analytes. Each probe type may not be cleaved as a result of presence of analytes aside from a single analyte that cleaves probe. Each plurality of probes 304a-c is immobilized upon a corresponding surface 308a-c. Surface 308a-c may include a sensor, i.e., may be a sensor surface. Alternatively or additionally, a sensor may be elsewhere disposed to detect a change in position or mobilization of probes. As is shown in FIG. 3, 3 different cleaving agents 312a-c are present within system 300 and located proximal surfaces 308a-c and probes 304a-c. However, only "b" analyte 316b is shown present in FIG. 3. As a result, only "b" cleaving agent 312b has cleaved only "b" probes 304b. In some cases, cleaving agents 312a-c and/or probes 304a-c may be attached to various surfaces 308a-c and their activity may be monitored separately, for example by using optical and/or electronic detection as described above. For example, in some cases, an optical system may include multiple ring resonators where each ring resonator may be functionalized with a different enzyme 312a-c (e.g., CRISPR CAS 12, CAS 13, etc.). These various cleaving agents 312a-c may be designed to be activated only when exposed to their specific analyte 316a-c target of interest. Once activated, each cleaving agent 312a-c, tethered to surface 308a-c, may cleave only probes 304a-c in its direct vicinity. Selective cleaving of only probes on one surface may lead to a detectable change (e.g. plasmon resonance optical readout or electronic transistor readout) related to only the surface 308b where cleavage occurred. In some applications, exemplary system 300 may permit different regions or different surfaces to detect different analytes from within a substantially shared sample without any interference or interdependence between detection of analytes. In some cases, a multi surface system, such as exemplary system 300 may be used substantially without any microfluidic or other physical separation of solutions carrying different analytes. In a nonlimiting example, RNA analytes 316a-c may be sensed using ring resonators, wherein different ring resonators on a chip may be functionalized by a CRISPR enzyme carrying a different crRNA sequence, allowing each ring to act as a sensor specific to a certain RNA sequence. In this example, it is possible for ring resonators to be exposed simultaneously to substantially the same solution containing analyte. In some embodiments, selective cleaving agents 312a-c may be specific to analytes (e.g., 316b). In some embodiments, probes may be cleaved by one or more cleaving agents 312a-c. Alternatively or additionally, each probe 304a-c may be cleaved only by a specific cleaving agent, which in turn may be specific to a specific cleaving agent, e.g., 316b. According to some embodiments, a probe 304a-c may have more than one cleavage site. A cleavage site may be a portion of a cleavable substance which corresponds to a cleaving agent. Cleavage site may include selective cleavage sites and general cleavage sites. In some cases, a selective cleavage site may be cleaved by a selective agent, e.g., 312b. In some cases, a general cleavage site may be cleaved by a general agent and/or multiple agents. In some cases, a cleavage site may be class specific. As used in this disclosure, a "class specific" cleavage site is a cleavage site that is selectively cleaved by a class or category of cleaving agents and/or analytes.

Figure 4:
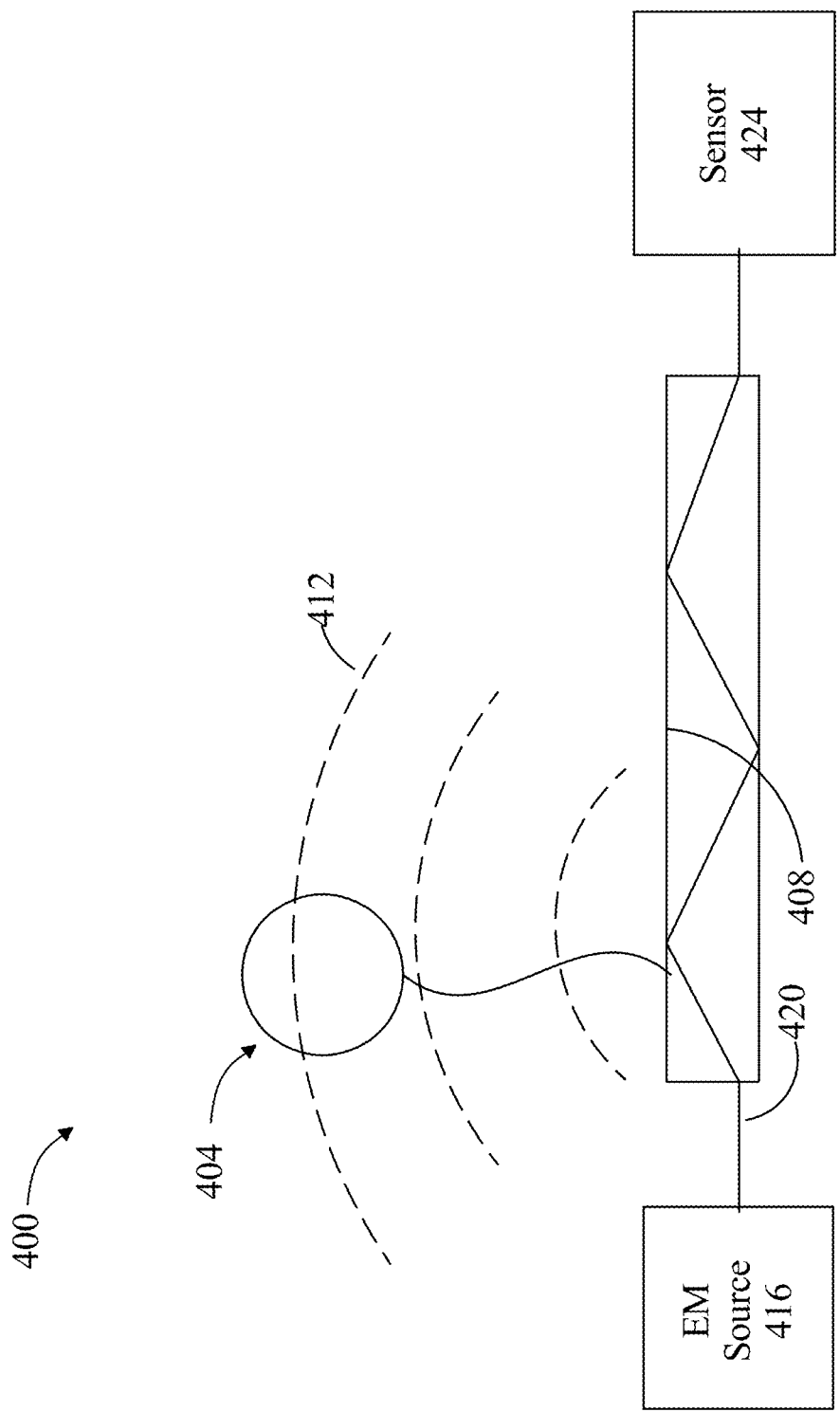
FIG. 4 is a block diagram illustrating an exemplary system for selective reaction catalyzation.

Referring now to FIG. 4, an exemplary system 400 for catalyzing a chemical reaction is illustrated. System 400 may include a reactant 404 which on a surface 408. In some cases, surface 408 may include a surface of a waveguide. Alternatively or additionally, surface 408 may include a surface of an optical, electronic, magnetic, MEMs or optoelectronic device. In one example, a chemical reaction at a waveguide may be catalyzed on a waveguide by way of an evanescent field 412 associated with the waveguide. In some cases, chemical reaction may be controlled by way of integrated photonics and at least a light source 416. In some cases, light source 416 may modulate intensity, output, and/or switch wavelengths to activate and control chemical reactions. In some cases, system 400 may control one or more of which reactions occur, where the reaction occurs, when the reaction occurs, and the like. Additionally or alternatively, reaction kinetics could be further controlled by controlling an intensity and/or wavelength of light 420, for example without limitation by using optical components such as ring resonators, optical switches, photonic crystals, Bragg gratings, LEDs, and lasers which are capable of introducing and controlling high-intensity light across a range of wavelengths. In some embodiments, system 400 may additionally include microelectromechanical systems (MEMS) components, which may be configured to aid in control of chemical reactions near surface 408, induce mixing, induce polymer folding, induce strain in the surface or in polymers attached to the surface, and the like. In some embodiments, system 400 may additionally include a sensor 424 which may be configured to detect in parallel or serially as chemical reactions are occurring, being catalyzed, controlled, and the like.

With continued reference to FIG. 4, in some embodiments, exemplary system 400 may be used to selectively catalyze one type of reaction, at a selected surface 408 (e.g. optical waveguide) and substantially not within rest of system 400 (e.g. microfluidic and chip surfaces). In some cases, catalyzed reaction upon a selected surface 408 may result in selective functionalization of the surface 408. Functionalization of surface 408 may include without limitation attaching antibodies, reporter probes, non-stick coatings, and the like.

Figure 5:
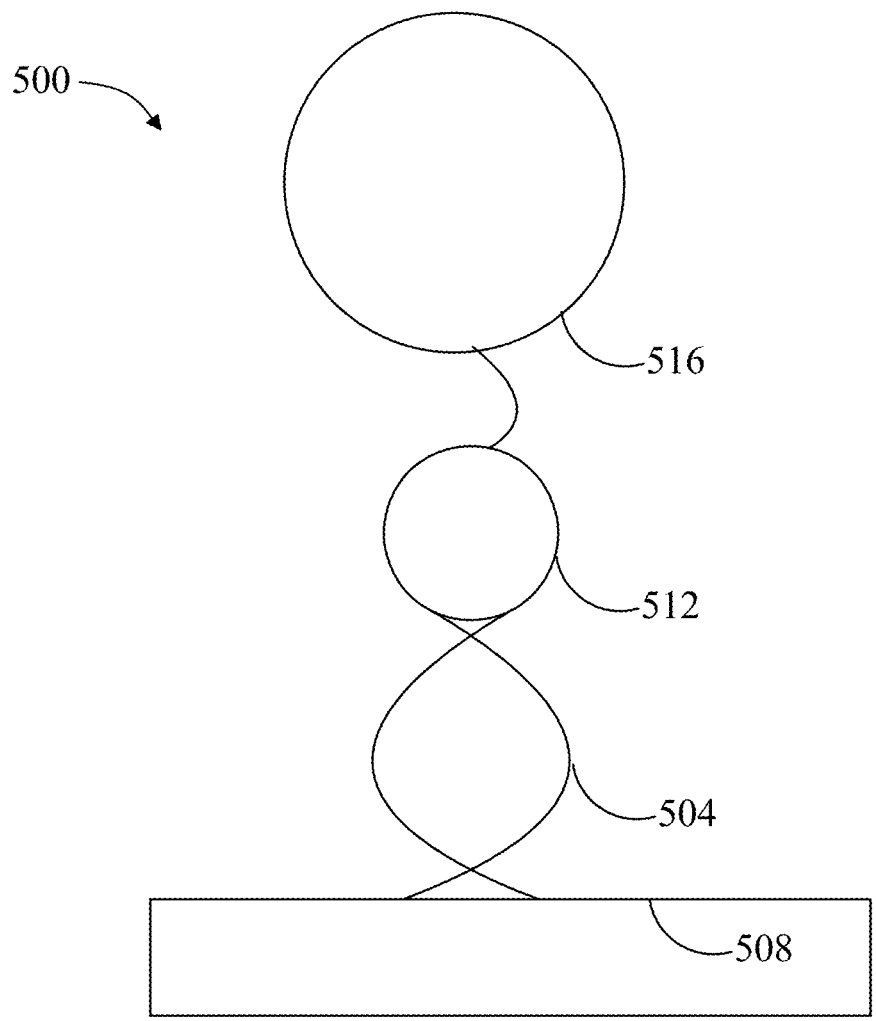
FIG. 5 is a block diagram of an exemplary system for monomer chain formation.

Referring now to FIG. 5, an exemplary system 500 for selective catalyzation and sensed formation of a polymer is illustrated. In some embodiments, system 500 may be used to build a monomer chain 504 onto a surface 508, for example one monomer at a time. Exemplary chains of monomers may include without limitation specific proteins, bioproteins, DNA, RNA, and the like. In some embodiments, building a monomer chain 504 may include attaching a monomer and capping the monomer with a capping agent 512 to control or otherwise limit further unintended growth to monomer chain. In a subsequent step capping agent 512 may be detached allowing for attachment of a next desired monomer. In some cases, capping agent 512 may be directly bonded to monomer such that it caps an end of the monomer that would normally be exposed for a next monomer addition or otherwise prevents the next monomer addition. Each step of monomer chain building, in some embodiments, has a certain yield, such that over hundreds or thousands of additions of monomer, cappings, and decappings, fidelity of a desired monomer chain may be undesirable. For example, a yield of 99% for each monomer adding step would yield a desired 100 monomer length chain only about 36.6% of the time. In some cases, systems and methods according to this disclosure may be employed to improve yield at each monomer addition step. In some embodiments, analyte may include a monomer. In some embodiments, analyte may include a capping agent.

Still referring to FIG. 5, embodiments disclosed herein may be used to build up sequences of monomers on a surface. In some embodiments, presence of each deposited monomer may be detected to ensure deposition of a correct monomer in a sequence; in this way, a yield of a desired monomer chain may be absolutely or nearly absolutely guaranteed, even for long sequences of monomers. Each deposition step may repeat deposition of the same monomer as a previous step or may be followed by deposition of a different monomer; at each monomer addition, sensing processes, which may include any sensing processes as described in this disclosure, may be used to determine if addition and/or deposition of a monomer to be added in that step has been successful and if sensing indicates monomer to be added in a current step and/or its capping agent is not present, the step may be repeated until a positive result is achieved. In this way uniform or heterogenous monomer chains may be constructed, including any desired sequence of monomers such as without limitation nucleotide sequences of RNA or DNA sequences, amino acid sequences such as peptides, proteins or the like, carbohydrate sequences, and/or any other sequences of monomers.

Further referring to FIG. 5, deposition may be performed using one or more mechanisms to ensure deposition of a desired and/or selected monomer in a given step. For instance and without limitation, deposition may be made through an opening that admits only a monomer of choice. This may be achieved, without limitation, by attachment of monomer to a bulky molecule; bulky molecule may have a shape corresponding to a current opening shape. Bulky molecule may include, without limitation, a capping agent, a high-contrast agent and/or probe, or the like. A shape and/or one or more dimensions of opening may be controlled, without limitation, using one or more MEMS devices and/or one or more similar devices.

Alternatively or additionally, and still referring to FIG. 5, deposition of a desired and/or selected monomer may be achieved by using microfluidics or another fluid flow control system such as without limitation an elution column to flow a single monomer past the reaction surface; as noted above, single monomer may be attached to a cap 516, an enzyme, or another bulky agent. The above-described deposition steps may be performed using a microfluidic cell, which may be employed to flow a different liquids in each deposition step, where each liquid only has the particular monomer to be added in that step.

Alternatively or additionally, and with further reference to FIG. 5, control of specific monomer that is added in any given step may be achieved using different wavelengths of light supplied to surface 508 where reaction is taking place. Different wavelengths may be delivered to surface, without limitation, using a evanescent field from a waveguide which is used as the reaction surface and/or other delivery using a waveguide, to catalyze addition of different monomers from solution. In an embodiment, each monomer may have a different catalytic wavelength associated with it. Catalytic wavelengths may include, without limitation, visible, ultraviolet, and/or near-infrared wavelengths. In an embodiment, a waveguide making up and/or connected with surface may be composed at least in part of silicon nitride ($Si_3N_4$), silicon dioxide ($SiO_2$), and/or any other material suitable for transmission and/or internal reflection of visible, ultraviolet, and/or near-infrared wavelengths. In an embodiment, controlling catalysis using optical means such as wavelength-selective, pulsed light, may be used to selectively control monomer buildup; for instance, a first wavelength may be pulsed until a first monomer catalyzed thereby has attached, which may be confirmed as described below, after which a second wavelength may be pulsed. Monomer-specific catalysis may alternatively or additionally be performed using chemical, enzymatic, or other catalysts specific to a monomer to be added in a given step; catalysts may include without limitation any catalyst that may occur to a person skilled in the art upon reviewing the entirety of this disclosure.

Still referring to FIG. 5, the above methodologies for selective application of monomers may be combined in any manner that may occur to a person skilled in the art upon reviewing the entirety of this disclosure. For instance, and without limitation, a catalyzing light may be limited to a specific site where one or more chains of monomers are being constructed; site may be limited to one monomer at a time, for instance, using an opening and/or microfluidic channel as described above to admit only one monomer, such as without limitation a monomer attached to a bulky molecule as described above. Similarly, microfluidic channels, openings shaped to admit only one monomer and/or bulky molecule, and monomer-specific wavelengths may be combined on each or any step to ensure deposition of a desired, chosen, and/or correct monomer for that step.

Further referring to FIG. 5, each deposition step described above may be followed in some embodiments by washing, which may include any washing step or modality described below. Washing may be performed, without limitation, prior to detection procedures and/or steps as described below; in some embodiments, this may prevent or make less probable false positive detections of labels and/or agents indicative of monomer attachment by removing any free-floating monomers that have not attached to monomer chain.

With continued reference to FIG. 5, capping agents 512 used for monomer buildup may be chemically bound to monomer 504 affixed to surface 508 from solution or may be pre-attached to the monomer 504. After deposition steps as described above and/or detection steps as described below, capping agent 512 may be removed chemically and/or by light, for instance and without limitation using a light-catalyzed reaction. In an embodiment, light used in a light-catalyzed de-capping process for a capping agent of a given monomer may have a distinct wavelength from light used to catalyze attachment of the given monomer; this may allow controlled and sequential attachment and de-capping to be performed, which may, as a non-limiting example, permit performance of detection steps, as described below, between attachment and de-capping steps. Chemical catalysis may be performed using any suitable chemical catalyst that may occur to persons skilled in the art upon reviewing the entirety of this disclosure, including without limitation enzymes, CRISPR enzymes, or the like; a chemical agent used to catalyze cap removal for a cap of a given monomer may be distinct from a chemical catalyst used to attach that monomer, which may, as a non-limiting example, ensure that de-capping and deposition may be controlled separately, permitting intervening sensing or other steps. Any other modality may be used to trigger and/or catalyze removal, including without limitation local and/or overall heating at and/or including reaction and/or deposition site.

In an embodiment, after monomer is added after sensing as described below, and/or after capping, for instance if a cap 516 was not attached to polymer and was free floating in solution, all excess monomers may be washed away with a rinse step. Cap 516 may then be removed, either prior to or after a sensing step, if used, using chemical, optical or other methods, for instance and without limitation as described above. Another monomer of choice, which may include any or all accompanying ingredients as described herein, including without limitation capping agents, enzymes that act as catalysts and/or as capping agents and enzymes simultaneously, high contrast labels and/or probes as described below, or the like, may subsequently be added until another monomer addition has been performed and/or sensed; for instance, a solution of one or more such ingredients may be flowed over a reaction region until a monomer addition event is sensed and/or accomplished, starting the process over again. A plurality of iterations may be performed in this way to build a monomer chain such as an amino acid and/or nucleotide sequence. Capping agents 512 used for monomer buildup may be chemically bound to monomer 504 affixed to surface 508 from solution or may be pre-attached to the monomer 504; for instance, capping agents may prevent attachment of monomers to undesired sites.

With continued reference to FIG. 5, in some cases, surface 508 includes a sensing surface with a sensor, which may include any sensing surface and/or sensor that may occur to a person skilled in the art upon reviewing the entirety of this disclosure, including without limitation sensors and/or sensing surfaces as described above, and a high contrast particle 516 and/or probe, which may include any high-contrast agent, particle, and/or probe that may occur to any person skilled in the art upon reviewing the entirety of this disclosure, including without limitation any high-contrast agent, particle, and/or probe as described above, may be bonded to capping agent 512 and/or monomer, and/or to surface adjacent to and/or at a reaction site for monomer deposition. High contrast particle 516 may allow monitoring of monomer chain building process, for example by methods described above, including those with reference to FIGS. 1-4. In an embodiment, sensing modalities as described herein may permit detecting what is on a surface; this may enable use of one or more high-contrast agents, particles, and/or probes, which may be collectively referred to for purposes of this disclosure as "labels," to label and/or distinguish each monomer and/or capping agent from other monomers and/or capping agents. Use of labels may enable monitoring in real time or near real time of monomer attachment; for instance and without limitation, one or more steps described above may be repeated, alternating with sensing steps, until a label corresponding to a chosen and/or desired monomer and/or its capping agent is detected. In an embodiment, label may be removed subsequently to detection of label, which may be accomplished, without limitation, using any process for detachment as described above, including chemical, heat and/or light catalysis, which may use distinct chemicals, wavelengths, or other catalytic processes and/or catalysts from attachment and/or de-capping catalysts. Alternatively or additionally, where label is attached to capping agent, de-capping may further accomplish detachment of label. Subsequent to de-capping, detachment of label, and/or rinsing, a detection step may be performed again to confirm absence of capping agent and/or label, prior to subsequent deposition steps. In an embodiment, where monomer and/or capping agent is an analyte as described above, detection may include introduction of a catalyst triggered by analyte as described above, causing probe detachment and detection; after successful detection, probes may be attached again to monomer chain and/or surface to prepare for subsequent attachment steps.

Further referring to FIG. 5, each label for a given monomer and/or capping agent thereof may be distinct from one or all of labels used with other monomers and/or capping agents. Detection step may include, without limitation, both attempts to detect a label corresponding to a currently desired and/or chosen monomer and/or capping agent thereof and attempts to detect one or more labels of distinct monomers; in an embodiment, where an incorrect label is detected, a monomer chain may be discarded, and errors may be caught and/or analyzed immediately for improvement of processes.

Still referring to FIG. 5, microfluidics may be used to wash away removed and/or unattached monomer and capping agents prior to a next step to ensure buildup of only a single monomer layer for each step of the process. In some examples, an optically active component 516 (e.g. plasmonic nanoparticle, quantum dot, molecule, etc.) may be affixed to capping agent 512 (e.g. enzyme). Since an optical signature of an optically active component 516 may be detected with certainty, for example by way of an optical waveguide as explained in detail above, yield of capping and decapping, or cap removal, steps may reach unity. For example, a process may include repeatedly flowing analyte via microfluidics until an optical signature of a capping agent 512 is detected. In some cases, this may also increase throughput as it would be unnecessary to continue flowing analyte associated with that monomer attachment step once the signature has been detected. Additionally or alternatively, light-active capping agents may be used for building a monomer chain 504 on a surface 508. In some cases, cap 512 may be any material (e.g. monomers, polymers, enzymes, etc.) that is catalyzed, transformed, and/or degraded by light. For example, one monomer may be added then quickly capped with a light-active capping agent 512 to prevent buildup of additional monomers. For a subsequent iteration of monomer deposition, capping agent 512 may be removed by exposing it to electromagnetic radiation (e.g. light in a waveguide). Additionally or alternatively, each monomer could be labeled with a different optically active component. If the signal of the optically active component is present after a monomer buildup step, it may confirm successful buildup. In some cases, light may be pulsed at a rate that may prevent multiple monomers from attaching in a single step. Optically active component 516 may also be chosen such that it would give a distinct optical signature of multiple optically-active components were present in a single buildup step, for instance and without limitation using a larger resonance shift.

With continued reference to FIG. 5, several methods may be implemented to further enhance capping and decapping techniques detailed above. For example, in some cases, it may be desirable to control deposition of capping agent 512 efficiently, for instance and without limitation using optically active component 516 to only desired surfaces such as a surface of a waveguide, or other sensing surface, as described above. Generally, a non-stick surface may be added to ensure capping agent 512 such as an enzyme is only deposited where desired, for instance on monomer 504. Additionally or alternatively, surface 508 may be covered with a protecting layer such as without limitation an SiO2 on a Si sensing surface. Trenches may be etched into protecting layer up to or into surface to give fluid access to surface 508 (and allow monomer chain build up in the trench) using common lithography techniques. Common deposition techniques (e.g. atomic layer deposition, etc.) may be used decrease the size of the opening in which the monomer buildup is occurring. In some cases, a size and/or shape of the opening may be engineered to ensure that only a single capping agent 512 will fit inside the opening. This may improve accuracy of detection of capping process and decapping process, for instance and without limitation by avoiding detecting stray free-floating or surface-adsorbed capping agents near sensing surface 508 but not actually bound to growing monomer chain 504. Deposition patterns may be conformal or may be angled in order to deposit non-stick material on the walls of the etched surfaces without filling in the etched trenches. An etch may be done all the way through a sensing surface and/or such that rinsing liquid can flow in a Z direction through the substrate and/or surface, washing vertical channel from any non-bound capping agents. Additionally or alternatively, wavelength-specific light may be used to control capping and/or decapping of monomers for monomer buildup 504. In one example, a wavelength may be selected that has minimal transmission through surface 508 for which monomers 504 are attached. Thus, capping-agent 512 may be activated for monomer deposition within trench, but not above the trench. This may prevent further growth of monomers 504 in unwanted regions of surface 508. More generally, controlled decapping of capping agents 512 may be activated in response to various triggers ranging from biological conditions (e.g. pH, reactive oxygen, etc.) to external stimuli (e.g. magnetic, thermal, electrical, etc.). In one example, monomer chain

504 may be built on a transistor to permit electrical manipulation of the monomer chain 504 building process.

With continued reference to FIG. 5, in another implementation, capping agents 512 may not be required for monomer buildup 504 on surface 508. For example, monomers may be added to monomer chain 504 on surface 508 by using pulses of light. In some cases, each monomer may interact with (e.g. be catalyzed by) a different wavelength of light, thus avoiding buildup of undesired monomers. In another example, light from a waveguide may be used to catalyze buildup of a functionalization layer on surface 508 of waveguide. In some cases, this may allow reporter probes or sensing targets (e.g., antibodies, antigens, etc.) to attach only to waveguide.

In some cases, and still referring to FIG. 5, sensitivity may be improved, as waveguide may represent a relatively small portion of surface 508. Alternatively or additionally, one implementation may involve reporter probes immobilized on all surfaces of system (e.g. on waveguide and other surfaces). In this case, waveguide may be functionalized with some component capable of capturing reporter probes (e.g. with a chemical bond) once cleaved by a cleaving component. In one non-limiting example, a gold nanoparticle may be biotinfunctionalized. The waveguide may have streptavidin capable of capturing and bonding to the biotin-functionalized gold nanoparticle. In one implementation, an antibody, antigen or another analyte (which itself may be a complex of a target analyte and another molecule) may act as a bridge to combine two or more separate molecules into a cleaving agent. Additionally, in some cases, a cleavage agent may be designed with a blocked active site, such that a blocking element can disassociate in presence of a correct analyte or when some change is sensed, for example without limitation pH, temperature, and the like. In some cases, dissociation of blocked active site may result from one or more environmental factors. Dissociation of blocked active site, in some cases, may cause resulting cleaving agent to cleave and thereby mobilize a secondary cleaving agent. Secondary cleaving agent may be selective and only activated in presence of an analyte. Once is presence of analyte secondary cleaving agent may cleave probes, which are detected. In this exemplary configuration and many others like it, multiple steps of cleaving may result in sensing of multiple conditions. In effect high-contrast cleavage detection as described may be used to combine multiple conditional elements, for example according to logical conditionals, such as "and," "or," "nor," "xor," and the like.

Further referring to FIG. 5, each step of deposition, capping, de-capping, sensing, washing, and/or modification to openings using MEMS or the like may be controlled and/or directed by a control circuit (not shown) which may include any combinational, sequential, asynchronous and/or synchronous circuit including logic circuit, digital circuit, and/or analog circuit elements, including without limitation any computing device as described in further detail below. Control circuit may be designed and/or configured to perform any method, method step, or sequence of method steps in any embodiment described in this disclosure, in any order and with any degree of repetition. For instance, control circuit may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Control circuit may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing to refer to FIG. 5, control circuit may control one or more components and/or devices, such as valves, pipettes, microfluidic channels, valves, or the like, light sources such as without limitation lasers, LEDS, or the like, sensors, and/or any other components for accomplishing any step described in this disclosure and/or any related step that may occur to persons skilled in the art upon reviewing the entirety of this disclosure.

Figure 6:
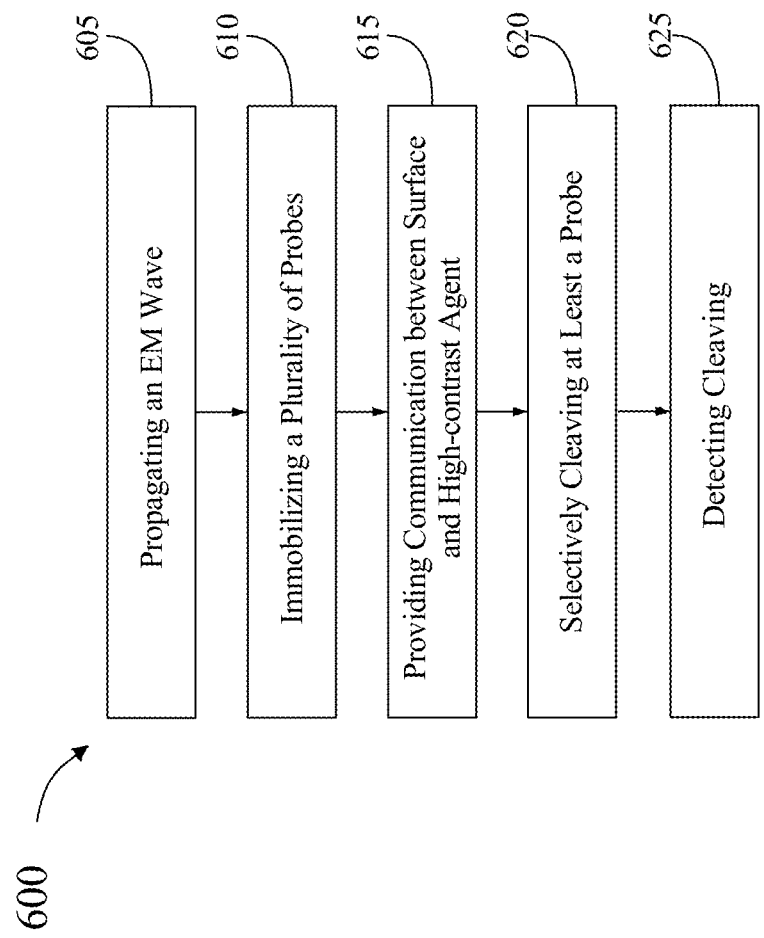
FIG. 6 is a flow diagram depicting an exemplary method of high-contrast cleavage detection.

Referring now to FIG. 6, a method 600 of high-contrast cleavage detection is illustrated by way of flow diagram. At step 605, a waveguide propagates an electromagnetic (EM) wave. A waveguide may include any waveguide described in this disclosure, for example in reference to FIGS. 1-5. An EM wave may include any EM wave described in this disclosure, for example in reference to FIGS. 1-5.

With continued reference to FIG. 6, at step 610, a surface of waveguide immobilizes a plurality of probes. Surface may include any surface described in this disclosure, including for example FIGS. 1-5. In some cases, a plurality of probes includes at least a probe that include a high-contrast agent. A probe may include any probe described in this disclosure, for example with reference to FIGS. 1-5. a high-contrast agent may include any high-contrast agent described in this disclosure, for example with reference to FIGS. 1-5. In some embodiments, analyte may include a monomer. Monomer may include any monomer described in this disclosure, for example with reference to FIGS. 1-5. In some cases, analyte may additionally include a capping agent. Capping agent may include any capping agent described in this disclosure, for example with reference to FIGS. 1-5.

With continued reference to FIG. 6, at step 615, surface may provide communication between EM wave and high-contrast agent. Communication may include any communication described in this disclosure, including for example with reference to FIGS. 1-5. In some embodiments, step 615 may additionally include propagating, using waveguide, an evanescent wave from the surface. In some embodiments, step 615 may additionally include propagating, using waveguide, surface plasmons upon surface. In some embodiments, step 615 may additionally include providing, using surface, optical communication between EM wave and high-contrast agent.

With continued reference to FIG. 6, at step 620, a primary cleaving agent selectively cleaves at least a probe of the plurality of probes. Primary cleaving agent may include any cleaving agent described in this disclosure, for example with reference to FIGS. 1-5. In some cases, selectively cleaving results from primary cleaving agent being in presence of an analyte. Analyte may include any analyte described in this disclosure, for example with reference to FIGS. 1-5. In some embodiment, cleaving agent may include an enzyme.

Enzyme may include any enzyme described in this disclosure, including for example with reference to FIGS. 1-5.

With continued reference to FIG. 6, at step 625, a sensor detects cleaving of at least a probe by way of EM wave. Sensor may include any sensor described in this disclosure, for example with reference to FIGS. 1-5. In some cases, sensor may be in communication with waveguide.

Still referring to FIG. 6, in some embodiments, method 600 may additionally include immobilizing, using surface, a secondary cleaving agent, cleaving, using primary cleaving agent in presence of analyte, the secondary cleaving agent, thereby mobilizing the secondary cleaving agent proximal plurality of probes, and cleaving, using the secondary cleaving agent, at least a probe of the plurality of probes. Secondary cleaving agent may include any cleaving agent described in this disclosure, for example with reference to FIGS. 1-5.

Still referring to FIG. 6, in some embodiments, method 600 may additionally include emitting, using a light source, a light having a wavelength, and catalyzing, using light, bonding of a monomer. Light source may include any light source described in this disclosure, including for example with reference to FIGS. 1-5.

Still referring to FIG. 6, in some embodiments, method 600 may additionally include flowing, using a microfluidic channel, a solution comprising analyte. Microfluidic channel may include any microfluidic channel described in this disclosure, for example with reference to FIGS. 1-5. Solution may include any solution described in this disclosure, for example with reference to FIGS. 1-5.

Figure 7:
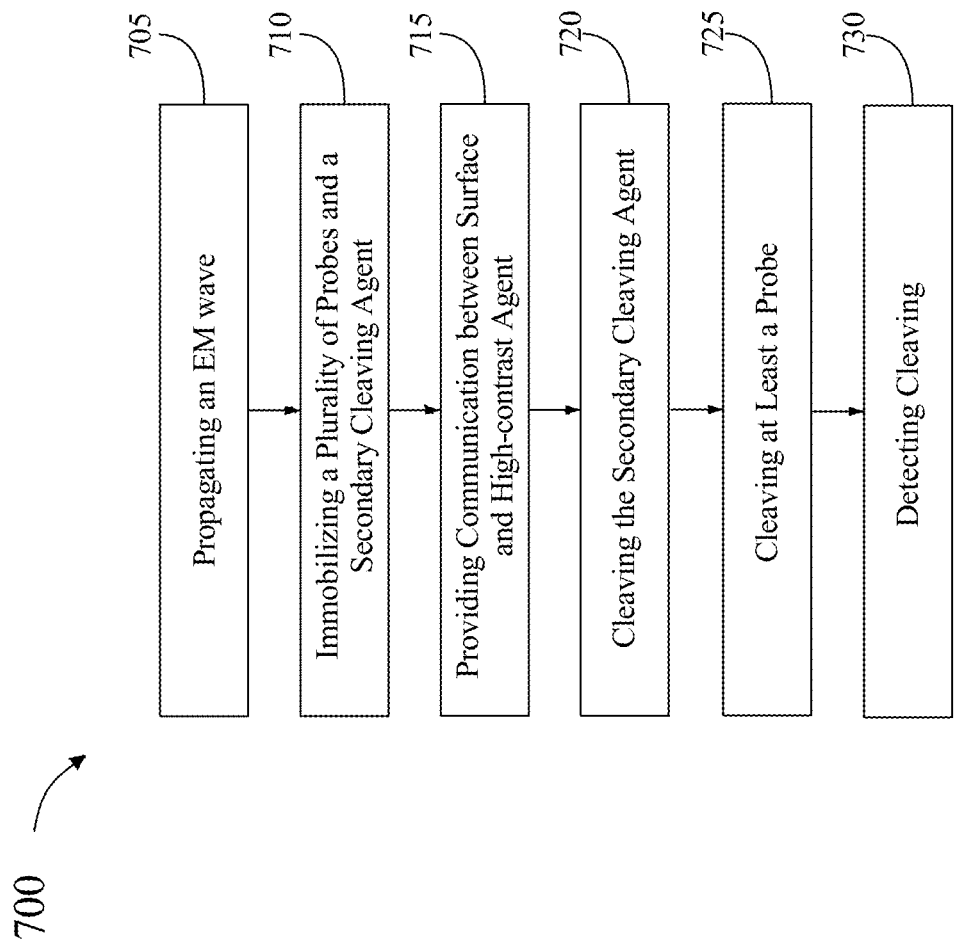
FIG. 7 is a flow diagram illustrating an exemplary method of cascading probe analyte detection.

Referring now to FIG. 7, a method 700 of cascading probe analyte detection is illustrated by way of a flow diagram. At step 705, method 700 may include propagating, using a waveguide, an electromagnetic (EM) wave. Waveguide may include any waveguide described in this disclosure, including in reference to FIGS. 1-6. EM wave may include any EM wave described in this disclosure, including in reference to FIGS. 1-6.

With continued reference to FIG. 7, at step 710, method 700 may additionally include immobilizing, using a surface of waveguide, a secondary cleaving agent and a plurality of probes wherein at least a probe of the plurality of probes comprises a high-contrast agent. Secondary cleaving agent may include any cleaving agent described in this disclosure, including with reference to FIGS. 1-6. Probes may include any probes described in this disclosure, including with reference to FIGS. 1-6. High contrast agent may include any high-contrast agent described in this disclosure, including with reference to FIGS. 1-6.

With continued reference to FIG. 7, at step 715, method 700 may additionally include providing, using surface, communication between EM wave and high-contrast agent.

With continued reference to FIG. 7, at step 720, method 700 may additionally include cleaving, using a primary cleaving agent in presence of a primary analyte, secondary cleaving agent, thereby mobilizing the secondary cleaving agent proximal plurality of probes. Primary analyte may include any analyte described in this disclosure, including with reference to FIGS. 1-6.

With continued reference to FIG. 7, at step 725, method 700 may additionally include cleaving, using secondary cleaving agent, at least a probe of plurality of probes. In some embodiments, method 700 may additionally include activate secondary cleaving agent with a secondary analyte.

With continued reference to FIG. 7, at step 730, method 700 may additionally include detecting, using a sensor in communication with waveguide, cleaving of at least a probe by way of EM wave. Sensor may include any sensor described in this disclosure, including with reference to FIGS. 1-6.

Still referring to FIG. 7, in some embodiments, method 700 may additionally include using primary cleaving agent, at least a probe. In some cases, at least a probe comprises a primary cleaving site associated with primary cleaving agent and a secondary cleaving site associated with secondary cleaving agent. In some additional cases, one or more of primary cleaving site and secondary cleaving site are class specific.

Still referring to FIG. 7, in some embodiments, method 700 may additionally include cleaving, using one or more of primary cleaving agent and secondary cleaving agent, a tertiary cleaving agent, thereby mobilizing the tertiary cleaving agent.

Figure 8:
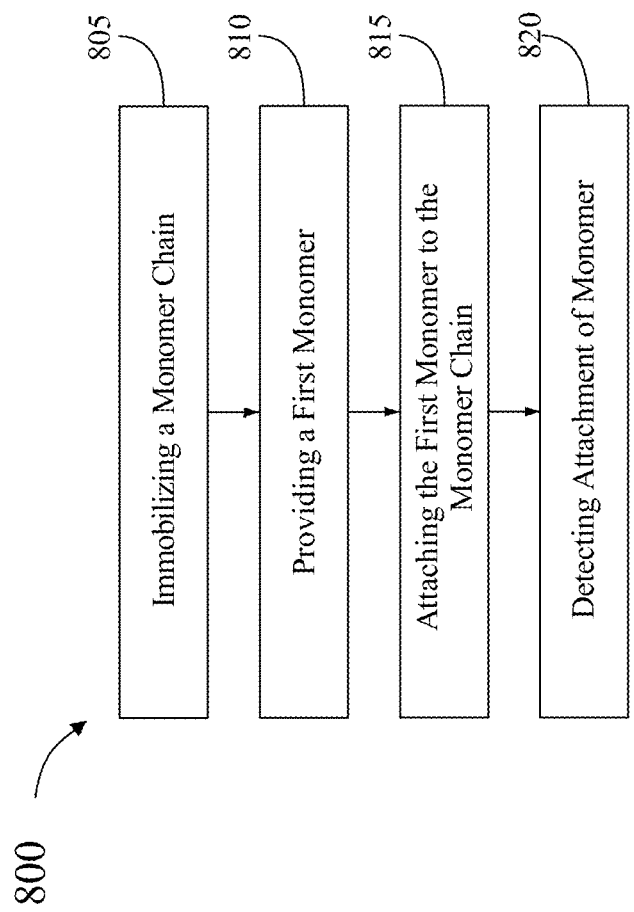
FIG. 8 is a flow diagram of an exemplary method of selective reaction catalyzation.

Referring now to FIG. 8, a method 800 of monomer chain formation is illustrated by way of a flow diagram. At step 805, method 800 may include immobilizing, using a surface of a waveguide, a monomer chain. Surface may include any surface described in this disclosure, including FIGS. 1-7. Waveguide may include any waveguide described in this disclosure, include with reference to FIGS. 1-7. Monomer chain may include any monomer chain described in this disclosure, including with reference to FIGS. 1-7.

With continued reference to FIG. 8, at step 810 method may include providing a first monomer. First monomer may include any monomer described in this disclosure. In some cases, first monomer may include a capping agent, including for example with reference to FIGS. 1-7. Capping agent may include any capping agent described in this disclosure, for example with reference to FIGS. 1-7. In some cases, capping agent may include or otherwise be bound to a high-contrast agent. High-contrast agent may include any high-contrast agent described in this disclosure, including for example with reference to FIGS. 1-7.

With continued reference to FIG. 8, at step 815, method 800 may include attaching first monomer to monomer chain. In some embodiments, attaching first monomer may include catalyzing a reaction between the first monomer and monomer chain. In some cases, catalyzing a reaction may include irradiating, using waveguide, monomer chain using an electromagnetic radiation.

With continued reference to FIG. 8 at step 820, method 800 may include detecting, using a sensor in communication with waveguide, attachment of monitor. Sensor may include any sensor described in this disclosure, including for example with reference to FIGS. 1-7. Detection of attachment of monitor may be performed using any process for detection of presence of an analyte as described above; analyte may include without limitation first monomer, capping agent, and/or any other element used in creation of monomer chain.

Still referring to FIG. 8, in some embodiments, method 800 may additionally include removing capping agent from first monomer; and detecting, using sensor, absence of high-contrast agent. In some cases, method 800 may additionally include providing a second monomer; and attaching the second monomer to the monomer chain. In some cases, removing capping agent may additionally include irradiating, using the waveguide, the monomer chain using an electromagnetic radiation.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve embodiments according to this disclosure. Accordingly, this description is meant to be taken only by way of example, and not to otherwise limit the scope of this invention.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
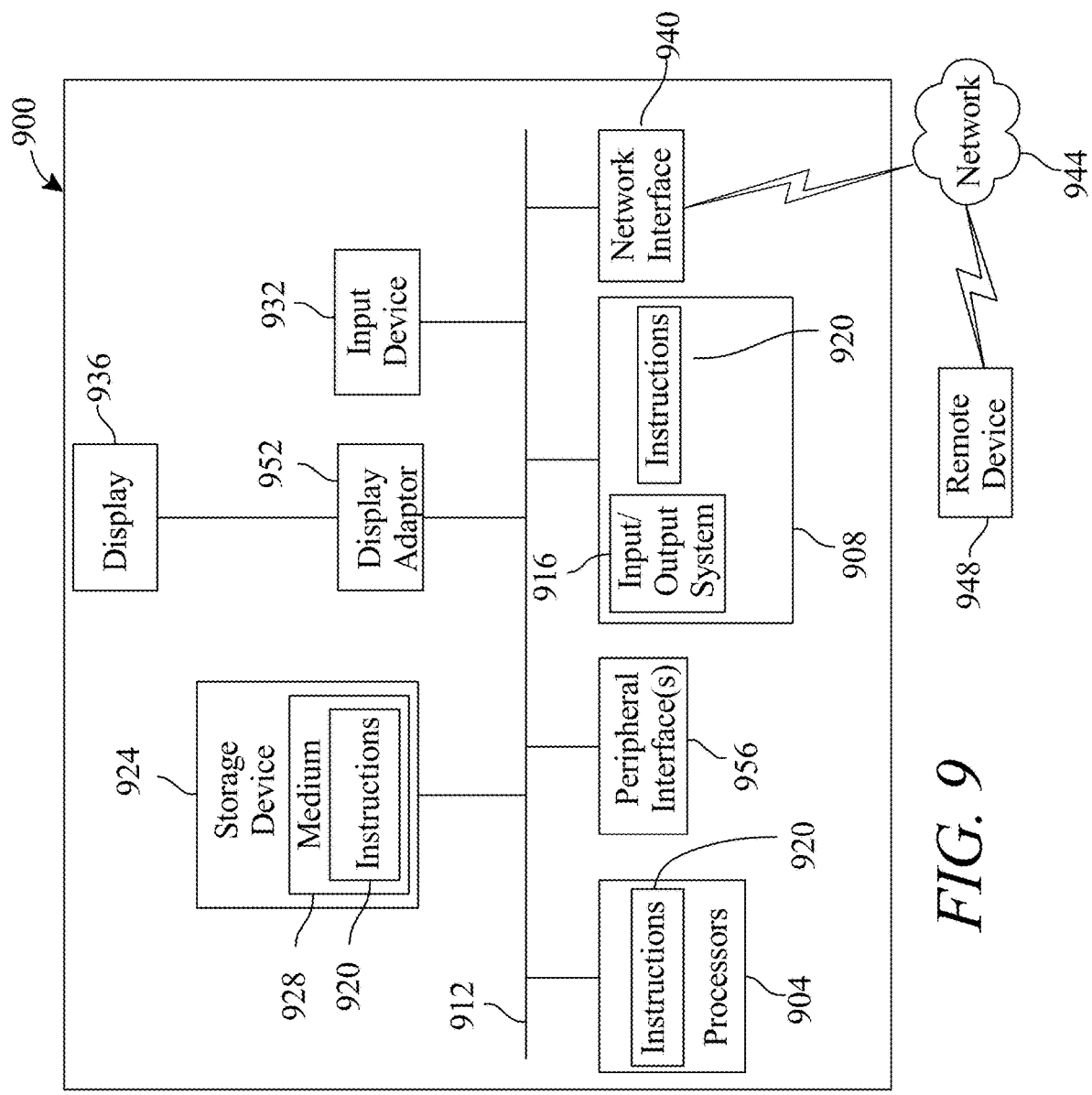
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of monomer chain formation comprising:
   immobilizing, using a surface of a waveguide, a monomer chain, wherein the surface of the waveguide further comprises a plurality of probes, wherein at least a probe of the plurality of probes comprises a high-contrast agent;
   providing a first monomer, wherein the first monomer comprises a capping agent;
   attaching the first monomer to the monomer chain; and
   detecting, using a sensor in communication with the waveguide, presence of the first monomer, wherein detecting further comprises:
   introducing a primary cleaving agent proximal the plurality of probes, wherein the primary cleaving agent is configured to selectively cleave the at least a probe as a result of the primary cleaving agent being in presence of an analyte; and
   introducing a secondary cleaving agent configured to selectively cleave at least an additional probe as a result of the secondary cleaving agent being in the presence of the analyte.

2. The method of claim 1, further comprising removing the capping agent from the first monomer.

3. The method of claim 2, further comprising:
   providing a second monomer; and
   attaching the second monomer to the monomer chain.

4. The method of claim 1, wherein the plurality of probes further comprises a plurality of ribonucleic acid (RNA) probes.

5. The method of claim 1, wherein the analyte comprises the first monomer.

6. The method of claim 1, wherein the analyte further comprises the capping agent.

7. The method of claim 1, wherein the waveguide is configured to provide communication between an EM wave and the high-contrast agent by propagating an evanescent wave from the surface.

8. The method of claim 1, wherein the surface is further configured to provide optical communication between an EM wave and the high-contrast agent.

9. The method of claim 1, wherein the high-contrast agent is attached to the monomer, and the method further comprises:
   detecting the high-contrast agent; and confirming attachment of the monomer as a function of the detection.

10. The method of claim 1, further comprising:
emitting, using a light source, a light having a wavelength; and
catalyzing, using the light, bonding of the monomer.

11. The method of claim 1, wherein the capping agent further comprises the high-contrast agent attached to the capping agent, and the method further comprises:
detecting the high-contrast agent; and
confirming attachment of the monomer as a function of the detection.

12. The method of claim 1, wherein the primary cleaving agent comprises a CRISPR enzyme.

13. The method of claim 1, further comprising flowing, using a microfluidic channel, a solution comprising the analyte.

14. The method of claim 1, wherein attaching the first monomer comprises catalyzing a reaction between the first monomer and the monomer chain.

15. The method of claim 14, wherein catalyzing the reaction comprises irradiating, using the waveguide, the monomer chain using an electromagnetic radiation.

16. The method of claim 1, further comprising removing the capping agent by irradiating, using the waveguide, the monomer chain using an electromagnetic radiation.

17. The method of claim 1, wherein the monomer comprises an amino acid.

18. The method of claim 1, wherein the monomer comprises a nucleic acid.

* * * * *